(12) United States Patent
Baynham et al.

(10) Patent No.: US 7,815,666 B2
(45) Date of Patent: Oct. 19, 2010

(54) DYNAMIC CERVICAL PLATE

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 732 days.

(21) Appl. No.: 11/624,575

(22) Filed: Jan. 18, 2007

(65) Prior Publication Data

US 2007/0276371 A1 Nov. 29, 2007

Related U.S. Application Data

(63) Continuation-in-part of application No. 10/776,369, filed on Feb. 10, 2004, now abandoned.

(51) Int. Cl.
 A61B 17/56 (2006.01)
 A61B 17/58 (2006.01)
 A61B 17/66 (2006.01)
 A61B 17/70 (2006.01)
 A61B 17/80 (2006.01)

(52) U.S. Cl. .......................... 606/280; 606/60; 606/70; 606/252; 606/257; 606/282; 606/286

(58) Field of Classification Search .................. 606/70, 606/287, 286, 71, 60, 281, 250, 280, 264, 606/289, 86 A, 293, 295, 296
See application file for complete search history.

(56) References Cited

U.S. PATENT DOCUMENTS

| 5,234,431 A * | 8/1993 | Keller ......................... 606/70 |
|---|---|---|
| 5,545,164 A | 8/1996 | Howland |
| 5,616,142 A | 4/1997 | Yuan et al. |
| 5,620,443 A | 4/1997 | Gertzbein et al. |
| 5,672,177 A | 9/1997 | Seldin |
| 5,702,395 A | 12/1997 | Hopf |
| 6,017,345 A | 1/2000 | Richelsoph |
| 6,136,002 A | 10/2000 | Shih et al. |
| 6,159,213 A | 12/2000 | Rogozinski |
| 6,402,756 B1 | 6/2002 | Ralph et al. |
| 6,689,134 B2 | 2/2004 | Ralph et al. |
| 7,041,105 B2 * | 5/2006 | Michelson ................... 606/71 |
| 2002/0188296 A1 | 12/2002 | Michelson |
| 2003/0060828 A1 | 3/2003 | Michelson |
| 2003/0130661 A1 * | 7/2003 | Osman ......................... 606/71 |
| 2004/0019353 A1 | 1/2004 | Freid et al. |

* cited by examiner

*Primary Examiner*—Thomas C Barrett
*Assistant Examiner*—Sameh Boles
(74) *Attorney, Agent, or Firm*—McHale & Slavin, P.A.

(57) ABSTRACT

A dynamic cervical plate has a ratchet and pawl mechanism that allows the cervical plate to post operatively shorten the length of the plate and maintain compression between adjacent vertebrae. The plate has an elongated shaft with teeth on one surface and a groove along each longitudinal edge. A lateral plate is attached on one end of the shaft. The plate has screw holes for connecting with the head of a spinal screw. Another lateral plate is slidably engaged in the longitudinal grooves along the shaft and has a spring clip acting as a pawl with the teeth on the shaft. The lateral sliding plate has screw holes on each side of the shaft. The clip is configured to span the screw holes to automatically engage and prevent screws from backing out of the holes.

19 Claims, 11 Drawing Sheets

DYNAMIC CERVICAL PLATE

CROSS-REFERENCE TO RELATED APPLICATIONS

This application is a continuation-in-part of U.S. patent application Ser. No. 10/776,369, filed Feb. 10, 2004, now abandoned the contents of which is herein incorporated by reference.

BACKGROUND OF THE INVENTION

This invention relates to the field of orthopedic surgery and, particularly, to the area of spinal implants for stabilizing the spatial relationship of vertebrae. The device is designed for use in the cervical region of the spine though one skilled in the art may use the device in other regions of the spine and other skeletal fixations.

DESCRIPTION OF THE PRIOR ART

Spinal plates are well known in the orthopedic art for fixing bones or bone fragments in a pre-selected spatial orientation. The plates are usually attached to the bones or bone fragments by screws designed to make a secure and long lasting connection not affected by the loads caused by normal activities of the host. Gertzbein et al, U.S. Pat. No. 5,620,443, teaches an adjustable cervical connector composed of dual rods spanning the distance between adjacent vertebrae. The rods carry at least two slidable transverse connectors which are attached to the vertebrae by spikes and pedicle screws thereby fixing the relationship of the bones. The connectors are immobilized on the rods by clamps.

Richelsoph, U.S. Pat. No. 6,017,345, teaches a spinal plate spanning the distance between adjacent vertebrae. The plate has screw holes in each end. The pedicle screws are inserted through the holes and allow for some movement.

Shih et al, U.S. Pat. No. 6,136,002, teaches a similar device to that of Gertzbein with the clamps screwed onto the elongated rods.

Published Patent Application U.S. 2003/0060828 A1 to Michelson teaches a cervical plate with at least two plate elements slidably connected together and fixed by a set screw. The contacting surfaces of the plate elements are formed with ratcheting to provide added security.

In all these prior art devices, the plate must be held in the selected position while the securing set screws or other fasteners are put in place and the final assembly is completed.

What is needed in the art is a dynamic cervical plate that may be adjusted to length, locked in place to provide compression, and will automatically shorten its length to maintain compression.

SUMMARY OF THE PRESENT INVENTION

Therefore, it is an objective of this invention to provide a cervical plate with an elongated shaft adapted to span the intervertebral space and having at least two screw receivers spaced along the length of the plate. The underside of the shaft includes integral serrations. The screw receivers each have countersunk apertures for accepting the heads of pedicle screws. Clips formed from a spring type material extend around the screw receivers and under the rod to cooperate with the serrations to allow the cervical plate to compress dynamically along the longitudinal axis of the rod when a compressive load is applied across the device. This load can be applied by the surgeon at the time of surgery and/or be produced during the healing phase by utilizing the compressive loads which occur during physical motion of the patient. The induction of a compressive load across the vertebral bodies to be fused, induces bone growth and when bone resorption occurs at the interface of the graft or implant and the vertebral bodies to be joined, those vertebral bodies are urged to move closer together, thus avoiding the formation of a gap therebetween and thereby acting to mitigate against pseudoarthrosis. The spring clips are also constructed to automatically engage the head portion of the pedicle screws upon complete insertion into the countersunk apertures. This construction prevents the screws from migrating out of the bone material during use of the device. In operation, as the screw head begins to enter the countersunk aperture the head forces a portion of the spring clip away from the aperture. As the head passes the clip, the clip returns to its original position to cover a portion of the screw head providing a positive lock for the screw.

Thus one objective of this invention is to provide a cervical plate having locking mechanism that is manually operated simultaneously with the positioning of the screw receivers along the plate to provide compression across an intervertebral space.

A further objective of this invention is to provide a cervical plate having an automatic locking mechanism having a retainer which extends over a portion of each screw hole to prevent back out migration of the screws.

Yet another objective of this invention is to provide a cervical plate having a guide rail on the plate shaft cooperating with the screw receivers to permit sliding connection between the screw receivers and the plate shaft.

Still another objective of this invention is to provide a cervical plate having a ratchet mechanism on the shaft and screw receivers to permit post-operative one-way movement shortening the distance between the screw receivers and maintaining compression across the intervertebral space.

Still yet another objective of this invention is to provide a cervical plate which includes a spring clip constructed to automatically engage a portion of each pedicle screw upon insertion into the cervical plate to prevent the pedicle screw from backing out of engagement with a bone.

An even further objective of this invention is to provide a cervical plate which includes a spring clip constructed to form part of the ratchet mechanism in addition to automatically engaging each pedicle screw upon insertion, whereby dynamic compression as well as screw migration is prevented.

Still a further objective of this invention is to provide a cervical plate having the ability to shorten in response to compressive loads to allow for bone portions to be fused to move close together to maintain or restore contact therebetween.

DETAILED DESCRIPTION OF THE INVENTION

Figure 1:
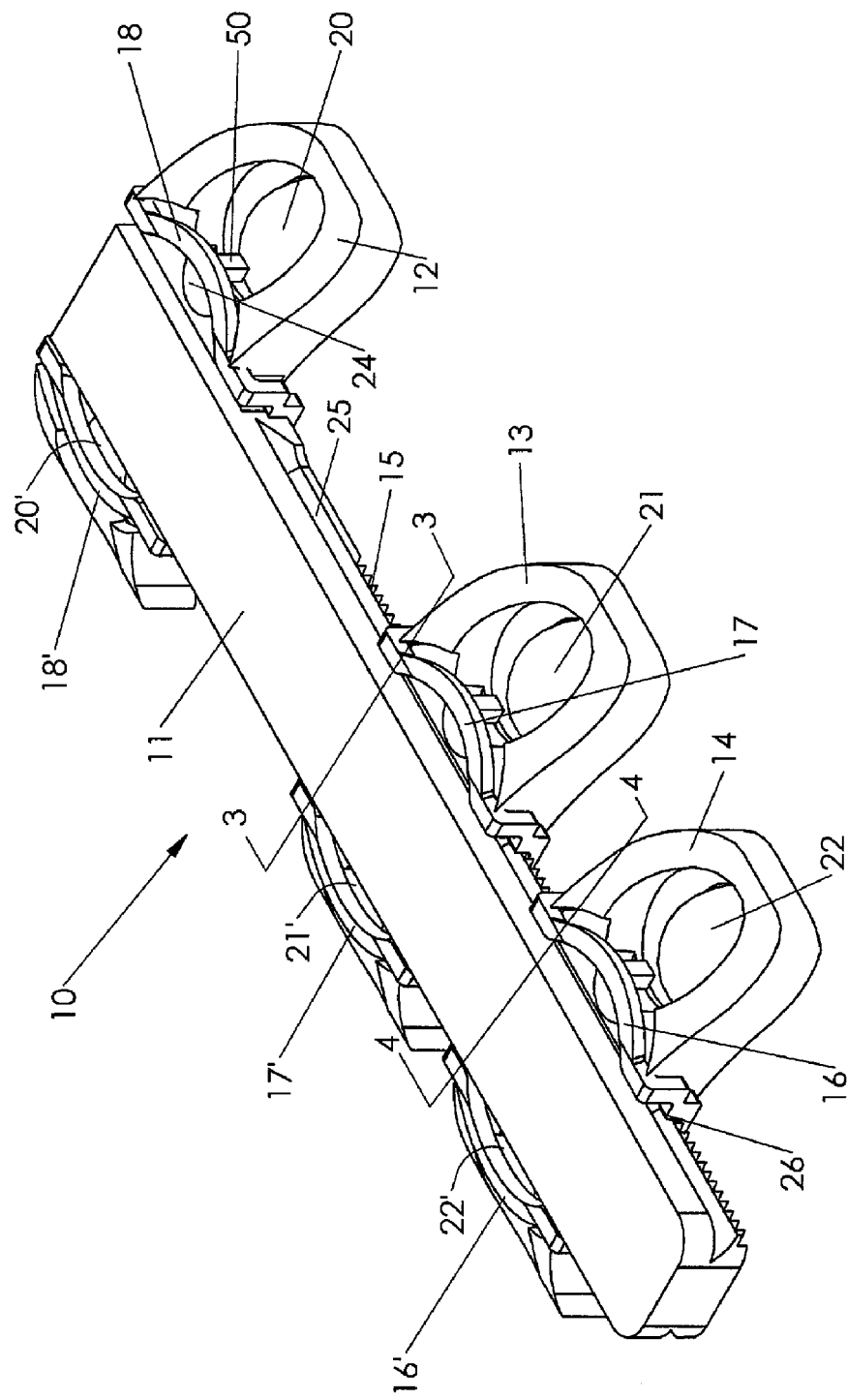
FIG. 1 is a perspective view of the cervical plate and screw receivers of this invention.
Figure 2:
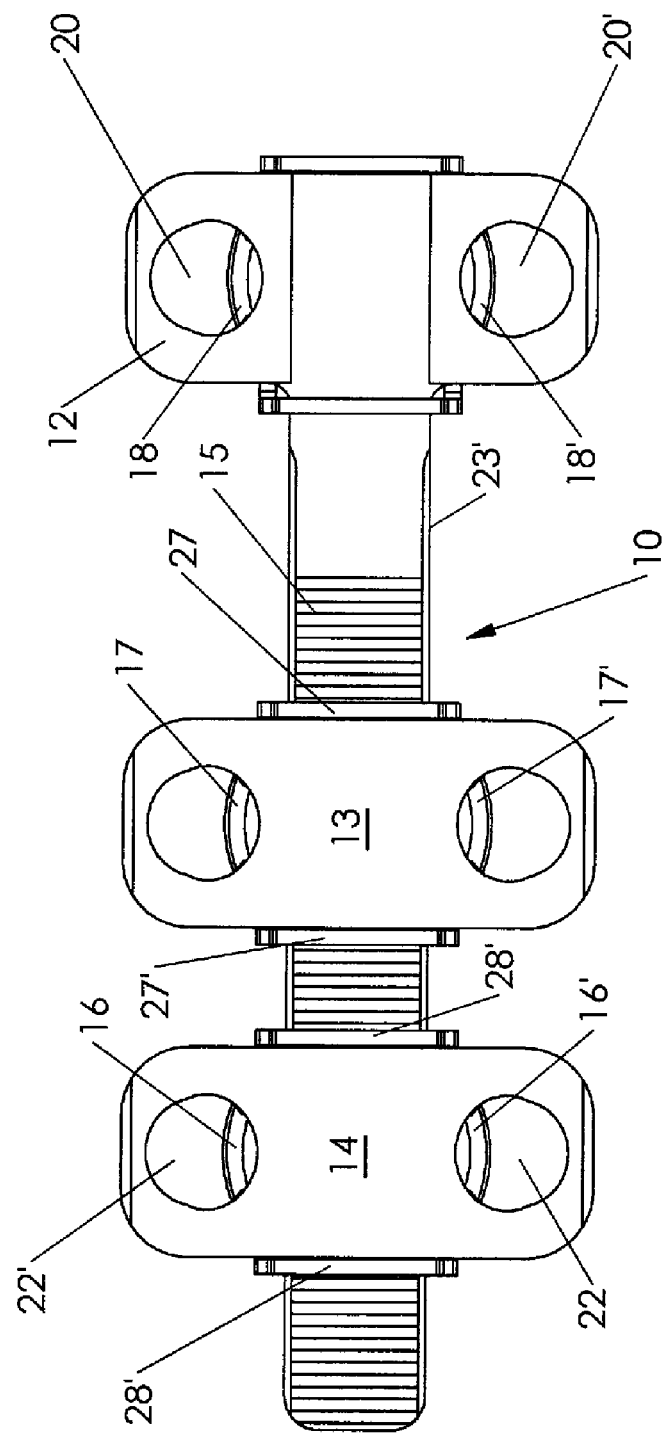
FIG. 2 is a bottom plan view of the cervical plate and screw receivers.

Referring to FIGS. 1-4, the cervical plate 10 has an elongated flat shaft that is made in different lengths but must be of a length to span, at least, the distance between two vertebrae. The plate has a lateral plate 12 fixed to one end and a free end. The plate has at least one and more preferably two countersunk apertures 20, 20' on each side of the plate for capturing the head of pedicle screws. Secured to the plate is a clip having ears 18, 18'. The clip is resilient and extends under the plate parallel but outside the periphery of the bar then rises vertically to the top of the plate and extends across the pedicle screw apertures 20, 20'. The portion that extends across the countersunk apertures 20, 20' are the ears 18, 18' for retaining the pedicle screws to prevent back-out. The clip is preferably constructed of a spring tempered metal to provide enough resiliency to allow flexing while the heads of the pedicle screws are seated in the aperture. Upon seating of the pedicle screw head in the countersunk aperture the ears of the clip automatically release on top of the screw heads. The clips may be constructed to apply a relatively constant pressure to the top portion of the screw head or alternatively there may be a small gap between the screw head and the ear. In either embodiment the screw is prevented from backing out of the bone. In one embodiment, the ears 18, 18' have wedges 50 which engage the edges of the screw heads as the screws are tightened to further lock the screws in place.

The bottom of the shaft has a row of teeth or serrations 15 formed across the longitudinal axis of the plate. The teeth are angled to form a ratchet allowing one-way movement of a bar from the free end toward the lateral bar at one end of the plate. In some instances, the teeth may be cut normal to the shaft. Along each longitudinal side of the shaft is a groove 23, 23' extending from the free end toward the lateral bar.

Slidably attached to the free end of the shaft is at least one and preferably two movable plate(s) 13, 14 having the same general construction. Therefore, reference to elements of one plate are the same as the other.

The plates 13, 14 have a distal surface which engages the vertebrae and are convexly curved to closely fit the curvature of the vertebrae. The plates have an aperture 21, 21' near each end with a channel 25 extending through the plate. The channel is approximately the same depth and includes a substantially conjugate shape to that of the shaft to provide a low profile to the assembled cervical plate. The opposite edges of the channel have shoulders 26, 26', shown in FIG. 3, that slide within the longitudinal grove 23, 23' in the plate. In a most preferred embodiment the channel and shoulders form a dovetail arrangement. This provides a close association between the surface of the bar channel and the ratchet teeth of the plate and prevents any substantial unwanted angular movement between the shaft and the plate(s).

Attached to bar 13 is a clip having a retainer 17, 17'. The clip has an elongated body with an oval shape when viewed from the top. The sides of the oval follow the edges of the depression so that the retainers 17, 17' are on the proximal surface of the bar. At least one side of the clips is preferably welded 99 or otherwise permanently attached to the respective side of the bars. The rounded ends of the oval form the screw retainers. The pawl portion 27, 28 of the clips extend across the shaft engaging the teeth 15 to form the ratchet. The pawls are formed by a raised flange 24, shown in FIG. 3.

Figure 3:
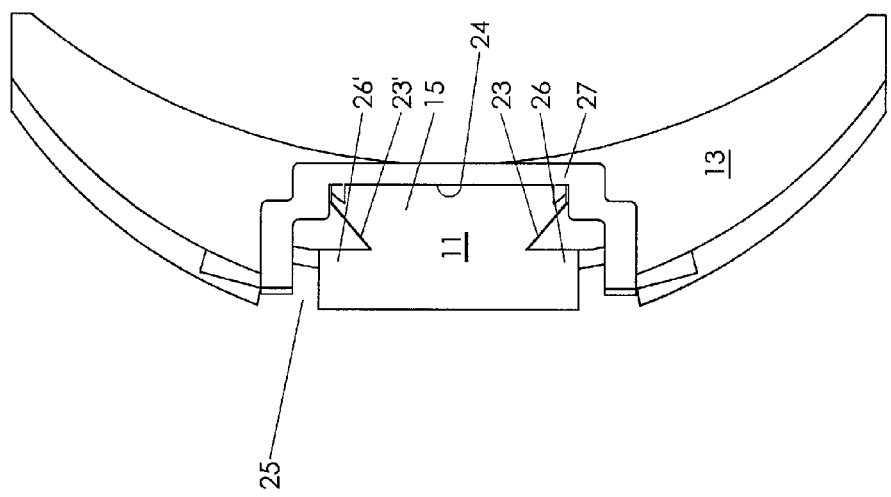
FIG. 3 is a cross section of the cervical plate, along line 3-3 of FIG. 1, with the clip unseated.
Figure 4:
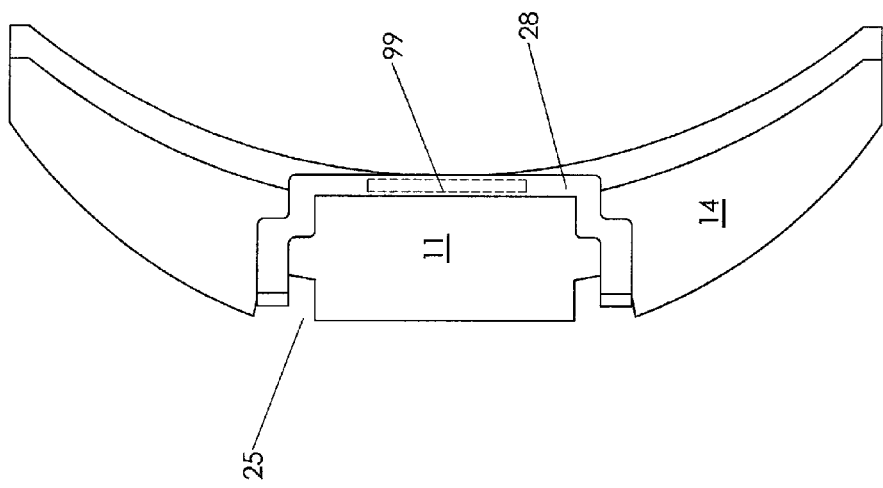
FIG. 4 is a cross section of the cervical plate, along line 4-4 of FIG. 1, with the clip seated in the ratchet.
Figure 5:
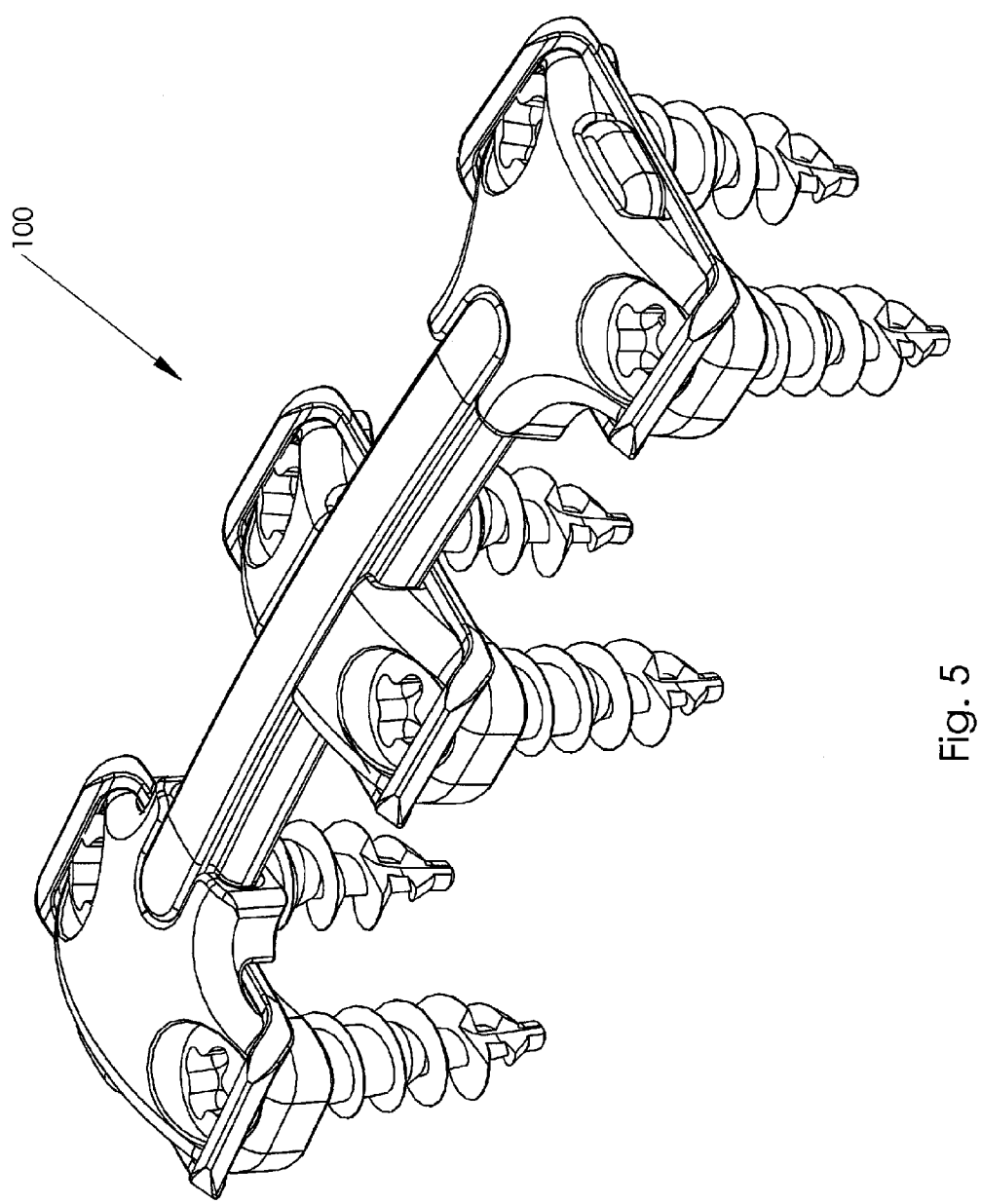
FIG. 5 is a perspective view of one embodiment of the instant invention, illustrated with the pedicle screws in place.
Figure 6:
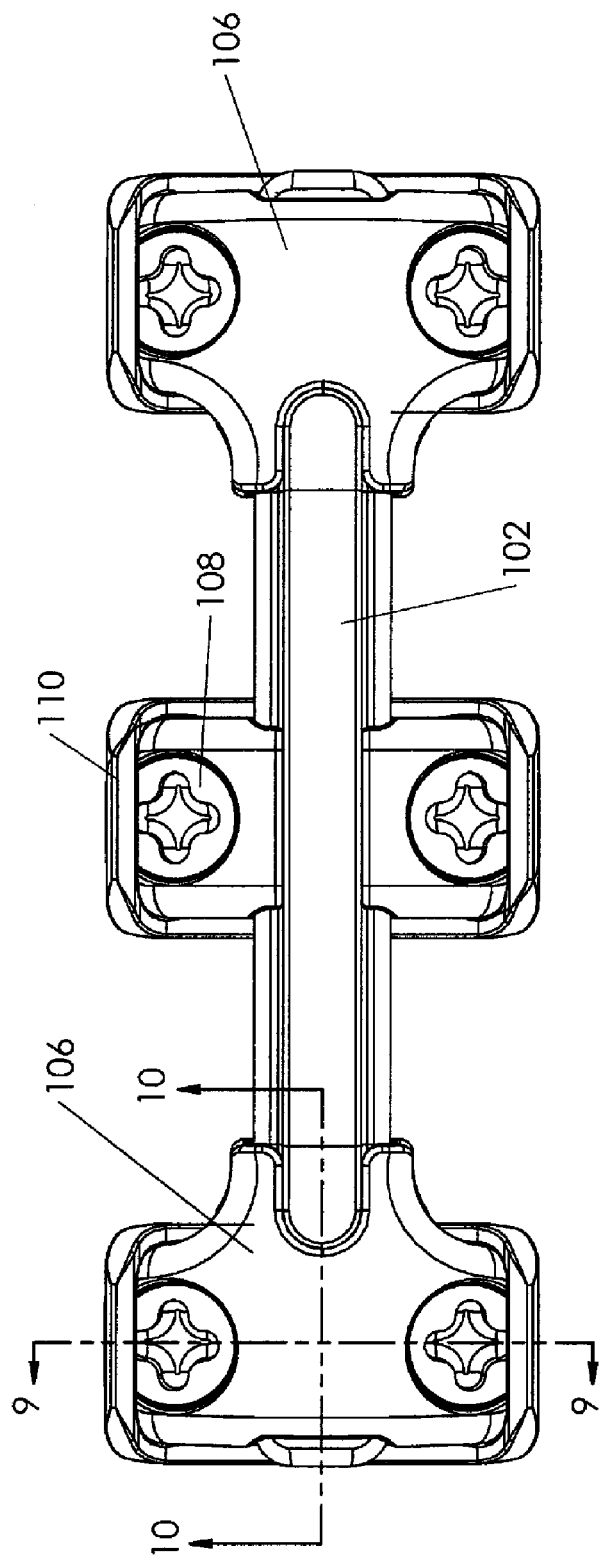
FIG. 6 is a top elevational view of the cervical plate shown in FIG. 5.
Figure 7:
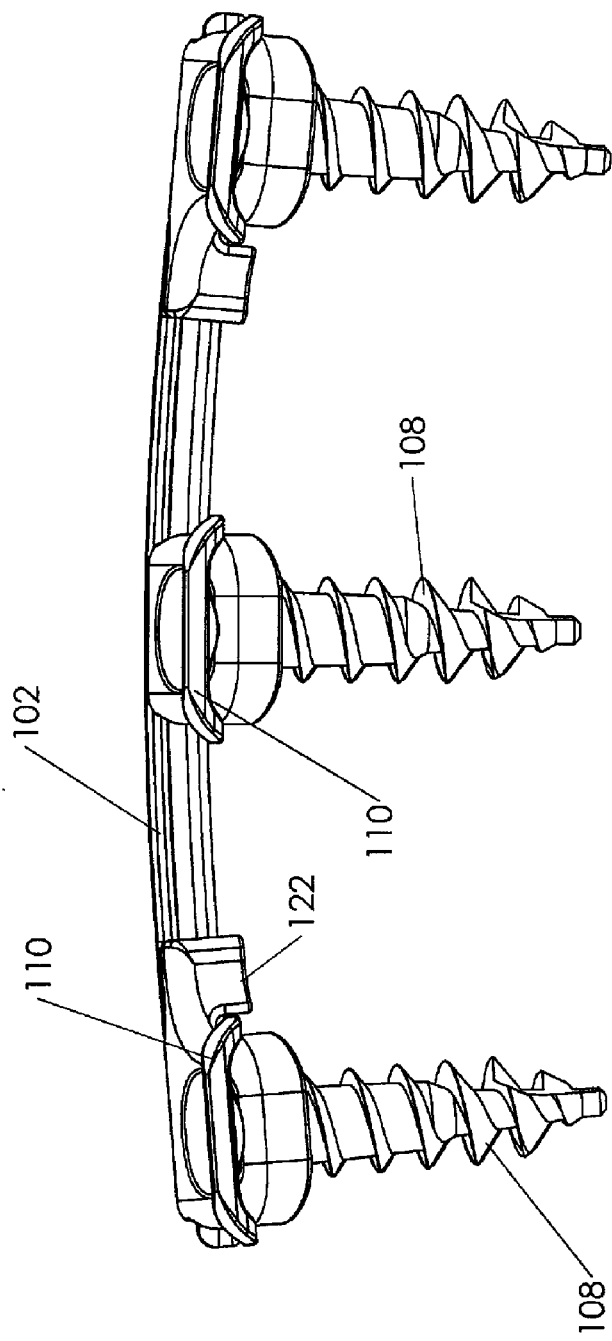
FIG. 7 is a side elevational view of the cervical plate shown in FIG. 5.
Figure 8:
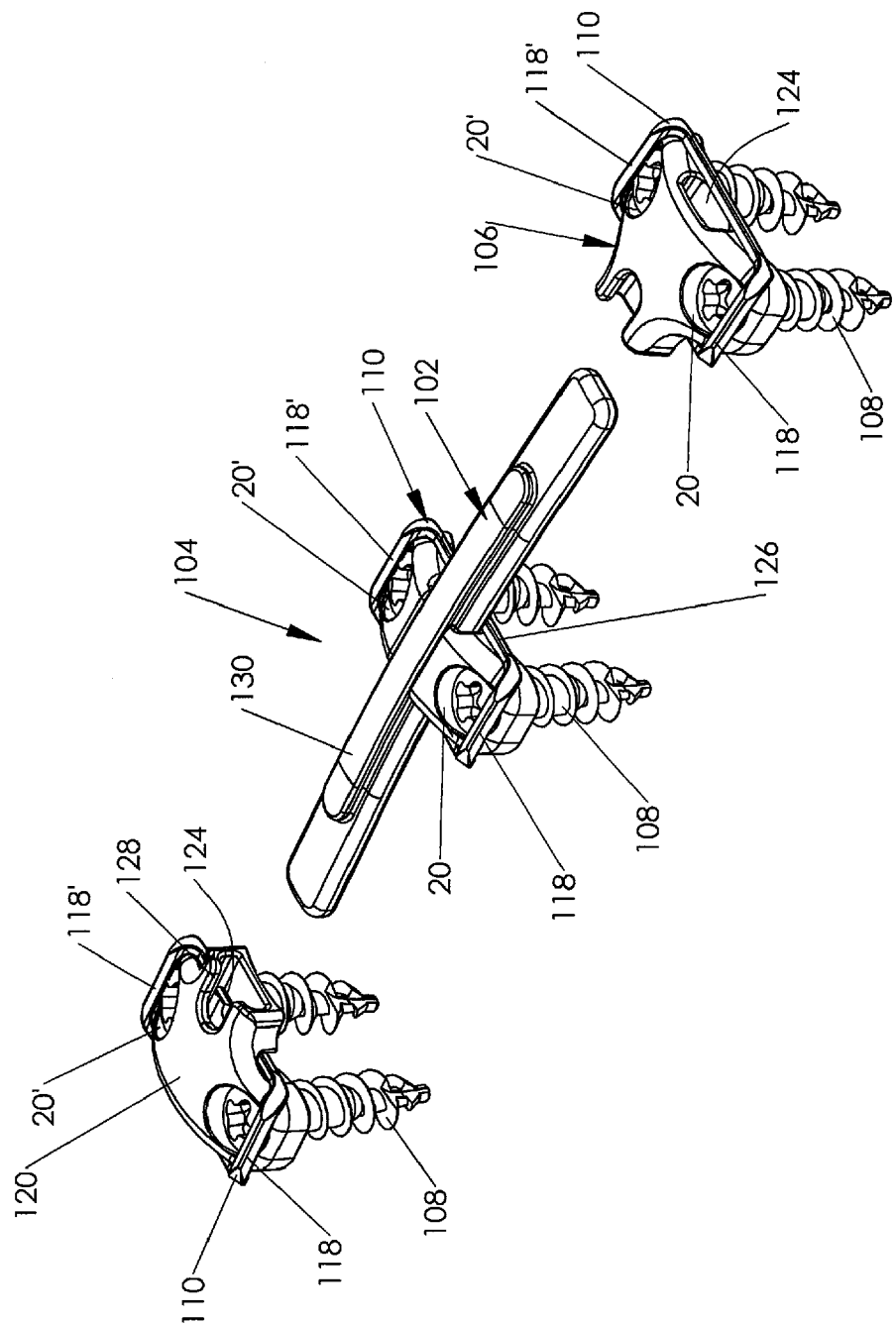
FIG. 8 is an exploded view of the cervical plate embodiment shown in FIG. 5.
Figure 9:
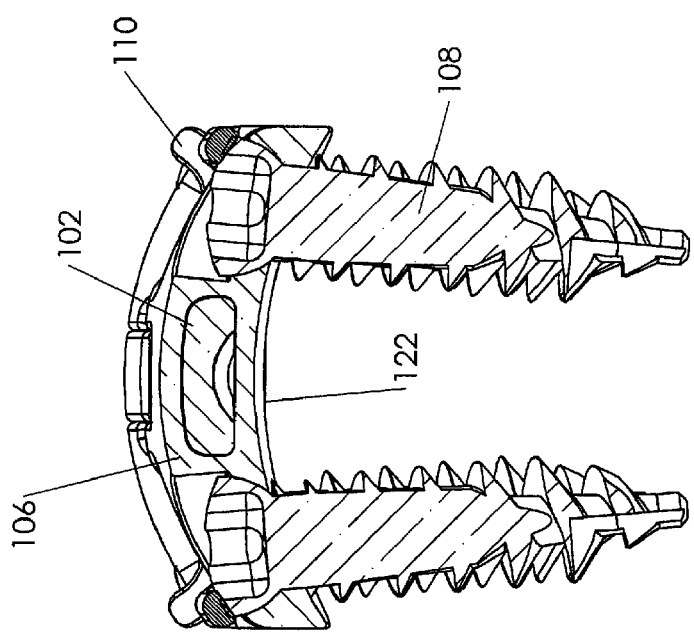
FIG. 9 is a section view taken along line 9-9 of FIG. 6.

In the preferred embodiment, the clips 16 and 17 have a flange that extends above the surfaces of the bars to engage the teeth 15 of the ratchet on the shaft. Of course, the clips may have pawls 27, 27' and 28, 28' on both sides of the bar, shown in FIG. 2. By flexing the clip with an instrument, the flange 24 can be disengaged from the ratchet teeth 15, as shown in FIG. 3, for initial adjustment.

In operation, the vertebrae are manipulated into the desired position and grafting material placed as required to compensate for removal of bone and/or disk material. The plate is placed on the spine and adjusted to provide some compression on the site to assist in the grafting of the spine. As the bars are slid along the shaft, the shoulders of the bars and the grooves on the shaft maintain a close fit between the pawls and the teeth on the shaft requiring the pawls to be deflected by the teeth. Once the bars are in the desired location and the flanges are seated in the teeth, the ratchet prevents retrograde movement of the bars away from the head. The pedicle screws are driven into the spine. As the screw heads engage the apertures the retainers are flexed to permit the screw heads to seat in the apertures and are thereafter automatically released to block back-out or migration of the screw.

It is well known that as the site heals and the adjacent vertebrae begin to graft together and as a result of the forces of gravity, there is some reduction in the span between the vertebrae. As this occurs the dynamic cervical plate can accommodate the reduction and maintain some compression because the shaft will move through the bars resulting in the clips moving from one ratchet tooth to the next automatically shortening the intervertebral distance. Of course, the pawls may be omitted, and the plate(s) may move in both directions along the shaft.

The second bar may be added to the free end of the plate to add stability to the compressed site and to reduce and equalize the pressure. Of course, the pawls may be omitted, and the plate may move in both directions within the bars.

Referring to FIGS. 5-9, an alternative embodiment of the cervical plate 100 is illustrated. The cervical plate 100 has an elongated flat shaft 102 that is made in different lengths but must be of a length sufficient to span, at least, the distance between two vertebrae. Slidably secured along the shaft 102 is a center lateral plate 104 and at least one and more preferably two end lateral plates(s) 106. The center lateral plate 104 has countersunk apertures 20, 20' on each side of the plate for capturing the head portion of pedicle screws 108. Mounted to the plate is a spring clip 110 having locks 118, 118'. The clip is resilient in construction and extends parallel along the side of the bar and under the shaft 102, then each end rises vertically to the top of the plate and extends across a portion of the pedicle screw apertures 20, 20'. The portion that extends across the countersunk apertures 20, 20' are the locks 118, 118' for retaining the pedicle screws to prevent loosening as well as back-out migration. The clip is preferably constructed of a spring tempered metal to provide enough resiliency to allow flexing while the heads of the pedicle screws are seated in the aperture. Upon seating of the pedicle screw head in the countersunk aperture the ears of the clip automatically release on top of the screw heads. The clips may be constructed to apply a relatively constant pressure to the top portion of the screw head or alternatively there may be a small gap between the screw head and the lock. In either embodiment the screw is prevented from backing out of the bone.

Figure 10:
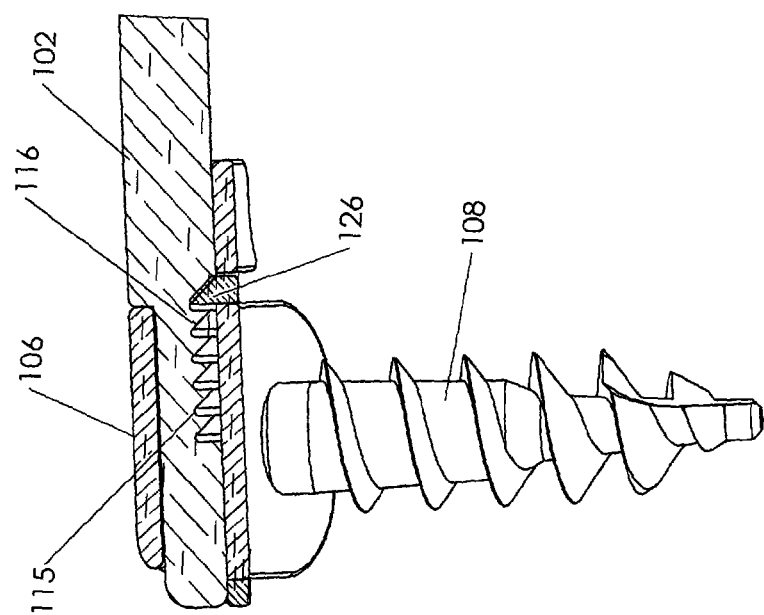
FIG. 10 is a section view taken along line 10-10 of FIG. 6.
Figure 11:
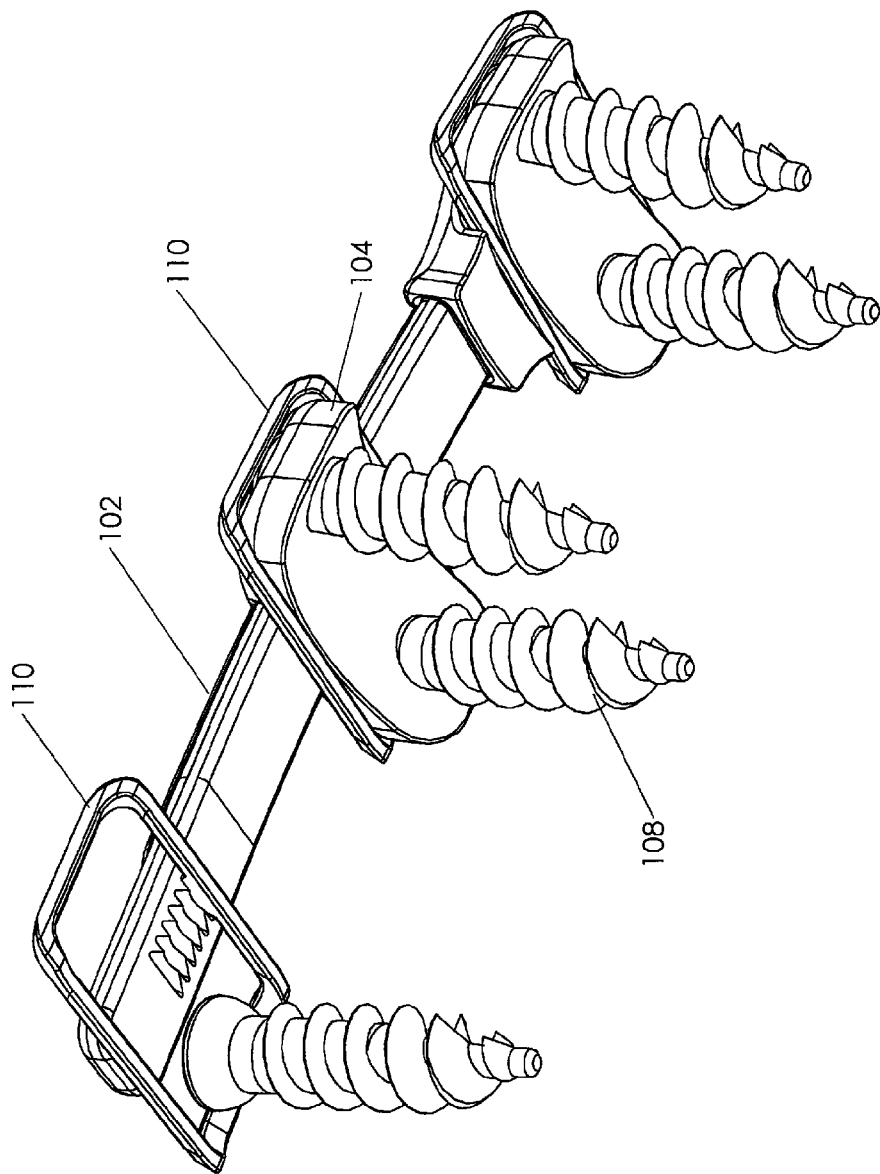
FIG. 11 is a partial bottom perspective view illustrated with one of the end plates and pedicle screws omitted.

The bottom of the shaft has a row of teeth or serrations 115 formed across the longitudinal axis of the plate. The teeth are angled to form a ratchet, as shown in FIG. 10, allowing one-way movement of a plate along the bar. In the most preferred embodiment, the teeth are cut normal to the shaft.

Slidably attached along the shaft is at least one and preferably two movable end plates 120 having the same general construction. Therefore, reference elements for each end element are the same. The slidable plates 120 have a distal surface 122 which engages the vertebrae and is convexly curved to closely fit the curvature of the vertebrae. Each plate includes an aperture 124 shaped and sized to approximate the size and shape of the shaft. This construction prevents unwanted movement between the plate(s) and the shaft and place the pawl portion 126 of the clip 110 in close approximation to the serrations on the shaft. The end plates may also include a contoured cut out portion 128 shaped to cooperate with a rib 130 formed integral to the shaft 102. The rib provides additional strength to the shaft while the cut-out cooperates with the rib to provide a low profile to the assembled cervical plate.

Mounted to the plate is a spring clip 110 having locks 118, 118'. The clip is resilient in construction and extends parallel along the side of the bar and under the shaft 102 then each end rises vertically to the top of the plate and extends across a portion of the pedicle screw apertures 20, 20'. The portion that extends across the countersunk apertures 20, 20' are the locks 118, 118' for retaining the pedicle screws to prevent loosening as well as back-out migration. The clip is preferably constructed of a spring tempered metal to provide enough resiliency to allow flexing while the heads of the pedicle screws are seated in the aperture. Upon seating of the pedicle screw head in the countersunk aperture the locks of the clip automatically release on top of the screw heads. The clips may be constructed to apply a relatively constant pressure to the top portion of the screw head or alternatively there may be a small gap between the screw head and the lock. In either embodiment the screw is prevented from backing out of the bone. At least one side of the clips is preferably welded or otherwise permanently attached to the respective side of the plate. The pawl portion 126 of the clips extend across the shaft engaging the teeth 115 to form the ratchet. In one embodiment, the clips 110 have a radiused top edge (FIG. 10) that cooperates with teeth 115 having at least one angled ramp surface 116 to define the ratchet assembly. By flexing the clip 110 with an instrument (not shown), the clip can be disengaged from the ratchet teeth 115 for initial adjustment or for controlled release of an engaged plate.

In operation, the vertebrae are manipulated into the desired position and grafting material placed as required to compensate for removal of bone and/or disk material. The plate is placed on the spine and adjusted to provide some compression on the site to assist in the grafting of the spine. As the plates are slid along the shaft, the conjugate shape of the apertures 124 and the shaft 102 maintain a close fit between the pawls 126 and the teeth 115 on the shaft requiring the pawls to be deflected by the teeth. Once the bars are in the desired location and the pawls are seated in the teeth, the ratchet prevents retrograde movement of the plates away from the head. The pedicle screws are driven into the spine. As the screw heads engage the apertures the locks 118 and 118' are flexed to permit the screw heads to seat in the apertures and are thereafter automatically released to block loosening and/or back out of the screw.

It is well known that as the site heals and the adjacent vertebrae begin to graft together and as a result of the forces of gravity, there is some reduction in the span between the vertebrae. As this occurs the dynamic cervical plate can accommodate the reduction and maintain some compression because the shaft will move through the plates resulting in the pawl portion of the clip moving from one ratchet tooth to the next automatically shortening the intervertebral distance. Of course, the pawls may be omitted, and the plate(s) may move in both directions along the shaft.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A dynamic spinal plate adapted to stabilize adjacent vertebrae comprising: an elongated shaft with a proximal surface and a distal surface, said elongated shaft having a first bar near one end adapted for connection with a vertebra, said shaft having an opposite end, at least a second bar movably attached near said opposite end, said first and second bars each having a screw hole adapted to seat a screw head, a first resilient spring clip attached to said second bar, wherein said elongated shaft has transverse teeth formed in said distal surface along the length thereof, said first resilient spring clip having a pawl portion seated between adjacent said transverse teeth and securing said second bar along the length of said elongated shaft thereby maintaining the space between said first bar and said second bar; said resilient spring clip having a retainer spanning said screw hole, whereby the first resilient spring clip will flex so as to allow the head of the screw to seat on said screw hole and upon seating of the screw head the first resilient spring clip will release on top of the screw head.

2. A dynamic spinal plate of claim 1 wherein said first bar is fixed to said shaft, said first bar extending transverse to said elongated shaft, screw holes in said first bar on each side of said elongated shaft, a second resilient spring clip attached to said first bar, said second resilient spring clip having a retainer spanning each of said screw holes, whereby the resilient spring clip will flex so as to allow the head of the screw to seat on said screw hole and upon seating of the screw head the resilient spring clip will release on top of the screw head.

3. A dynamic spinal plate of claim 2 wherein said second bar extends transverse to said elongated shaft, screw holes in said second bar on each side of said elongated shaft, said first resilient spring clip attached to said second bar having a retainer spanning each of said screw holes.

4. A dynamic spinal plate of claim 2 wherein said elongated shaft has a longitudinal groove along each side, said second bar including a central depression with shoulders on each side, each of said shoulders engaging said longitudinal groove along each side of said shaft for slidable movement of said second bar along said shaft with said central depression in close contact with said elongated shaft.

5. A dynamic spinal plate of claim 2 wherein said shaft has transverse teeth formed in said distal surface along the length thereof, said first resilient spring clip attached to said second bar having a pawl portion seated between adjacent teeth.

6. A dynamic spinal plate of claim 3 wherein said elongated shaft has a longitudinal groove along each side, said second bar including a central depression with shoulders on each side, each of said shoulders engaging said longitudinal groove along each side of said shaft for slidable movement of said second bar along said shaft with said central depression in close contact with said elongated shaft.

7. A dynamic spinal plate of claim 3 wherein a third bar is slidably attached near said opposite end of said elongated shaft, said third bar extends transverse to said elongated shaft, screw holes in said third bar on each side of said elongated shaft, a third resilient spring clip fixed to said third bar having a retainer spanning each of said screw holes.

8. A dynamic spinal plate of claim 3 wherein said shaft has transverse teeth formed in said distal surface along the length thereof, said first resilient spring clip attached to said second bar having a pawl portion seated between adjacent teeth.

9. A dynamic spinal plate of claim 7 wherein said elongated shaft has a longitudinal groove along each side, said second bar and said third bar each including a central depression with shoulders on each side, each of said shoulders engaging said longitudinal groove along each side of said shaft for slidable movement of said third bar along said shaft with said central depression in close contact with said elongated shaft.

10. A dynamic spinal plate of claim 7 wherein said shaft has transverse teeth formed in said distal surface along the length thereof, each said resilient spring clip attached to said second and said third bar having a pawl portion seated between adjacent teeth.

11. A dynamic spinal plate of claim 1 wherein said elongated shaft has a longitudinal groove along each side, said second bar including a central depression with shoulders on each side, each of said shoulders engaging said longitudinal groove along each side of said shaft for slidable movement of said second bar along said shaft with said central depression in close contact with said elongated shaft.

12. A dynamic spinal plate of claim 11 wherein said shaft has transverse teeth formed in said distal surface along the length thereof, said first resilient spring clip attached to said second bar having a pawl portion seated between adjacent teeth.

13. A dynamic spinal plate of claim 1 wherein said transverse teeth are angled toward said opposite end whereby said shaft may advance through said second bar shortening the distance between said first bar and said second bar, said pawl portion and said transverse teeth preventing lengthening said distance.

14. A dynamic spinal plate of claim 13 wherein said first bar is fixed to said shaft, said first bar extending transverse to said elongated shaft, screw holes in said first bar on each side of said elongated shaft, a second resilient spring clip attached to said first bar, said second resilient spring clip having a retainer spanning each of said screw holes, said second bar extends transverse to said elongated shaft, screw holes in said second bar on each side of said elongated shaft, said first resilient spring clip attached to said second bar having a retainer spanning each of said screw holes, said elongated shaft having a longitudinal groove along each side, said second bar including a central depression with shoulders on each side, each of said shoulders engaging said longitudinal groove along each side of said shaft for slidable movement of said second bar along said shaft with said central depression in close contact with said elongated shaft.

15. A dynamic spinal plate of claim 14 wherein a third bar is slidably attached near said opposite end of said elongated shaft, said third bar extends transverse to said elongated shaft, screw holes in said third bar on each side of said elongated shaft, a third resilient spring clip fixed to said third bar having a retainer spanning each of said screw holes, said third resilient spring clip fixed to said third bar including a pawl portion, whereby said shaft may advance through said third bar shortening the distance between said first bar, said second bar, and said third bar, said pawl portion of said third resilient spring clip fixed to said third bar and said transverse teeth preventing lengthening said distance.

16. A dynamic spinal plate adapted to stabilize vertebrae comprising an elongated shaft with a proximal surface and a distal surface, said shaft having one bar fixed at one end adapted for connection with a vertebra, said bar extending laterally normal to said elongated shaft, screw holes in said one bar on each side of said elongated shaft, said shaft having an opposite free end, said shaft having a set of transverse teeth formed on said distal surface, at least a second bar movably attached near said free end of said plate, said second bar adapted for connection with an adjacent vertebra, said second bar extending laterally normal to said elongated shaft, screw holes in said second bar on each side of said elongated shaft, said second bar including an attached resilient spring clip, said resilient spring clip having a flange engaging said teeth and securing said second bar along the length of said plate thereby maintaining the space between said one bar and said second bar, whereby upon a flexing of the resilient spring clip with an instrument the flange can be disengaged from said teeth and repositioned at a different position along said set of teeth; said resilient spring clip having a retainer spanning said screw hole, whereby the resilient spring clip will flex so as to allow a head of screw to seat on said screw holes and upon seating of the screw head the resilient spring clip will release on top of the screw head.

17. A dynamic spinal plate of claim 16 wherein said elongated shaft has a longitudinal groove along each side, said second bar including a central depression with shoulders on each side, each of said shoulders engaging said longitudinal groove along each side of said shaft for slidable movement of said second bar along said shaft with said central depression in close contact with said elongated shaft.

18. A dynamic spinal plate of claim 17 wherein said transverse teeth are angled toward said opposite end whereby said shaft may advance through said second bar shortening the distance between said first bar and said second bar, said flange and said transverse teeth preventing lengthening said distance.

19. A dynamic spinal plate of claim 18 including a third bar movably attached near said free end, said third bar having a central depression with shoulders on each side, each of said shoulders engaging said longitudinal groove along each side of said shaft for slidable movement of said third bar along said shaft with said central depression in close contact with said elongated shaft, said third bar including an additional attached resilient spring clip, said additional resilient spring clip having a flange engaging said teeth and securing said third bar along the length of said plate thereby maintaining the space between said one bar and said second bar.

* * * * *